United States Patent
Wang et al.

(10) Patent No.: US 9,221,853 B2
(45) Date of Patent: Dec. 29, 2015

(54) GLYPHOSATE DIMETHYLAMINE SALT CRYSTAL, PREPARATION METHOD AND USE THEREOF

(75) Inventors: Wei Wang, Jiande (CN); Shuguang Zhou, Jiande (CN); Long Qin, Jiande (CN); Bufan Ren, Jiande (CN); Zhigang Qian, Jiande (CN); Tao Liu, Jiande (CN); Huiling She, Jiande (CN); Yaxian Zhang, Jiande (CN)

(73) Assignee: ZHEJIANG WYNCA CHEMICAL INDUSTRY GROUP CO., LTD., Jiande, Zhejiang Province (CN)

( * ) Notice: Subject to any disclaimer, the term of this patent is extended or adjusted under 35 U.S.C. 154(b) by 799 days.

(21) Appl. No.: 13/514,464

(22) PCT Filed: Oct. 25, 2010

(86) PCT No.: PCT/CN2010/001692
§ 371 (c)(1),
(2), (4) Date: Jul. 26, 2012

(87) PCT Pub. No.: WO2011/069324
PCT Pub. Date: Jun. 16, 2011

(65) Prior Publication Data
US 2015/0307528 A1    Oct. 29, 2015

(30) Foreign Application Priority Data
Dec. 9, 2009   (CN) .......................... 2009 1 0154988

(51) Int. Cl.
| A01N 57/20 | (2006.01) |
| C07F 9/38 | (2006.01) |
| C07C 211/04 | (2006.01) |
| A01N 33/04 | (2006.01) |

(52) U.S. Cl.
CPC . *C07F 9/38* (2013.01); *A01N 33/04* (2013.01); *A01N 57/20* (2013.01); *C07C 211/04* (2013.01); *C07B 2200/13* (2013.01)

(58) Field of Classification Search
None
See application file for complete search history.

(56) References Cited

U.S. PATENT DOCUMENTS

| 3,799,758 A * | 3/1974 | Franz ............... C07F 9/3813 504/195 |
| 5,324,708 A | 6/1994 | Moreno et al. |

FOREIGN PATENT DOCUMENTS

| CN | 1260344 A | 7/2000 |
| CN | 1340508 A | 3/2002 |
| CN | 1445234 A | 10/2003 |
| CN | 1958594 A | 5/2007 |
| CN | 101186622 A | 5/2008 |
| CN | 101723973 A | 6/2010 |

* cited by examiner

*Primary Examiner* — Mina Haghighatian
*Assistant Examiner* — Erin Hirt
(74) *Attorney, Agent, or Firm* — Clark & Elbing LLP

(57) ABSTRACT

This invention provides the herbicidal active ingredient, a dimethylamine salt crystal of N-phosphonomethyl glycine (glyphosate), its preparation process and a solid formulation containing the crystalline dimethylamine salt of glyphosate as well as its application. Said preparation process comprises adding glyphosate and a suitable amount of solvent into a conventional reactor and introducing a dimethylamine gas for reaction, wherein the reaction temperature is controlled between 5 and 90° C. After the completion of the reaction, the temperature is reduced slowly to a certain value, a crystalline dimethylamine salt of glyphosate is precipitated (or precipitated after a crystal seed is added).

26 Claims, 3 Drawing Sheets

GLYPHOSATE DIMETHYLAMINE SALT CRYSTAL, PREPARATION METHOD AND USE THEREOF

CROSS-REFERENCE TO RELATED APPLICATIONS

This application is the U.S. National Stage filing under 35 U.S.C. §371 of International Application No. PCT/CN2010/001692, filed Oct. 25, 2010, which claims the benefit of Chinese Patent Application No. 200910154988.6, filed Dec. 9, 2009.

TECHNICAL FIELD

This invention relates to a solid herbicide applied to agriculture and other locations in need of controlling weeds or undesirable plants, its production method and application. Specifically, this invention relates to a crystalline dimethylamine salt of the herbicidally efficacious ingredient N-phosphonomethyl glycine (glyphosate) and its production method, a herbicidal composition comprising said crystal and the production and use thereof.

BACKGROUND ART

Glyphosate is a broad-spectrum non-selective herbicide. Since glyphosate has a low solubility in water (12 g/L, 25° C.), in practice, glyphosate is generally formulated into a water-soluble salt. The soluble salts of glyphosate most widely applied at present are mainly isopropyl amine salt, ammonium salts, potassium salt, dimethylamine salts and so on, wherein the dimethylamine salt of glyphosate is the species having the best herbicidal effect and broadest global application among the soluble salts of glyphosate.

A dimethylamine salt of glyphosate generally refers to the monodimethylamine salt of glyphosate which has the following chemical formula:

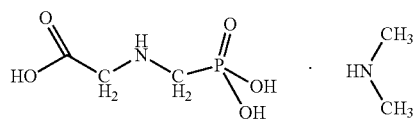

The formulations of the salts of glyphosate now are still mainly the aqueous formulations. Since aqueous formulations contain a large amount of water, there is much inconvenience in terms of packaging, transportation, storage and so on, and in the meantime, the costs increase. As the market develops and has the increasing demands, there are more and more urgent technical requirements for producing solid formulations with a high content of the glyphosate salts.

At present, the glyphosate salts suitable for the production of solid formulations are mainly the ammonium salts of glyphosate, and the ammonium salts of glyphosate are usually used to prepare the solid formulation products of glyphosate salts, and the industrialized production of granules has been accomplished.

There are only the aqueous formulations at present as the formulations of dimethylamine salt of glyphosate, and it is one of the major aqueous formulation products of US DOW AGROSCIENCES LLC. Up to now, there have not been the relevant reports about a solid formulation of dimethylamine salt of glyphosate.

The Chinese patent application CN 99119971.5 filed by the present applicant discloses a process of industrially producing ammonium salt granules of glyphosate with glyphosate as the starting material, which comprises: to a pressure pan equipped with a stirrer, glyphosate is added, while liquid ammonia is also introduced for reaction, and the weight ratio of glyphosate to liquid ammonia is 1:0.5-1:5; the reaction heat is removed during reaction in time; after the completion of the reaction, the bleeder valve is opened so that the product, ammonium glyphosate, is pressed into a pressure relief tank for granulation to prepare the granules of ammonium glyphosate.

The Chinese patent application CN 00125934.2 filed by the present applicant discloses a process: the solvent, an alcohol, an ether, an aromatic hydrocarbon, an alkane or an organic solvent-water mixture with a water content of less than 25% (w/w) is added to a reactor, and glyphosate and ammonia gas are also added for reaction at a temperature of 10-50° C.; the reaction mixture is cooled to 15-20° C., and then the precipitated crystals are taken therefrom and dried to obtain the product, ammonium glyphosate.

The Chinese patent application CN 02141788.1 filed by the present applicant discloses a process for producing ammonium glyphosate by a gas-liquid-solid three phase reaction, which comprises: glyphosate and water are added to a reactor equipped with a stirrer, and then ammonia gas is introduced for reaction; after the completion of reaction, an aqueous solution of ammonium glyphosate is formed; the solubility of ammonium glyphosate in this system is reduced by the way like adding a water-soluble organic solvent such as methanol, ethanol or methylal into the system so as to precipitate the crystalline solid ammonium glyphosate.

The Chinese patent application CN 200610154750.X filed by the present applicant discloses a process: a soluble salt and a suitable amount of water are added into a reactor at first; the solution is sufficiently stirred to dissolve the salt and then to the salt solution, glyphosate is added and the mixture is stirred to evenly disperse the glyphosate; the reaction temperature is controlled; isopropyl amine is added; after the completion of the reaction, a solid isopropyl amine salt of glyphosate is obtained by crystallization and filtration.

The Chinese patent application CN 200610154745.9 filed by the present applicant discloses a process: glyphosate and a suitable amount of water are mixed under sufficient stirring, then a base containing potassium cation is added for reaction; the reaction temperature is controlled, and then reduce the temperature, and a potassium salt of glyphosate is obtained by crystallization and another time of drying. Also, a process is disclosed therein: a solid glyphosate and a suitable amount of water are mixed under sufficient stirring, then a base containing potassium cation is added for reaction; the reaction mixture is directly dried to obtain potassium glyphosate.

Although there are a number of methods for producing solid glyphosate salts nowadays, the use of these methods to prepare solid dimethylamine salt of glyphosate in industry has the following difficulties: first, the dimethylamine salt of glyphosate has the solubility in water much bigger than that of glyphosate, and even has a certain solubility in some organic solvents and is not easy to crystallize so that it is also more difficult to search a suitable solvent for precipitating it by crystallization; second, the aqueous solution of the dimethylamine salt of glyphosate has a very high viscosity and is characterized in forming gel when it achieves a higher concentration, which causes considerable difficulties in its precipitation by crystallization.

In light of the technical difficulties and problems in the prior art as mentioned above, the present inventor has conducted the investigations deeply and carefully to obtain a crystalline dimethylamine salt of glyphosate and its industrial production process, and a solid herbicidal composition and formulation containing said crystal, and thus fulfills this invention.

CONTENTS OF INVENTION

Therefore, the present invention provides a crystalline dimethylamine salt of glyphosate and its industrial production process, and a solid herbicidal composition and herbicidal formulation containing the crystalline dimethylamine salt of glyphosate as well as the production process and use thereof.

In summary, the present invention provides the following technical solutions:

1. The compound, dimethylamine salt of N-phosphonomethyl glycine (i.e., dimethylamine salt of glyphosate) shown in formula (I), in crystalline form:

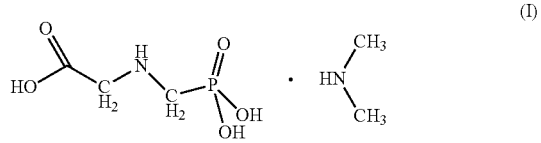

characterized in that the X-ray powder diffraction pattern of this crystal has at least one or more peaks at the angle $2\theta(°)$ ($\pm 0.2$) of 14.26, 20.44, 20.47, 25.19, 27.49 and 33.51.

2. The crystalline dimethylamine salt of glyphosate according to the technical solution 1, characterized in that the X-ray powder diffraction pattern of this crystal has peaks at the angle $2\theta(°)$ ($\pm 0.2$) of 14.26, 20.44, 20.47, 25.19, 27.49 and 33.51.

3. The crystalline dimethylamine salt of glyphosate according to the technical solution 1 or 2, characterized in that the X-ray powder diffraction pattern of this crystal further comprises one or more peaks at the angle $2\theta(°)$ ($\pm 0.2$) of 14.22, 14.29, 20.37, 20.41, 20.51, 23.38, 25.15, 25.22, 33.17, 33.21 and 42.23.

4. The crystalline dimethylamine salt of glyphosate according to the technical solution 3, characterized in that the X-ray powder diffraction pattern of this crystal further comprises one or more peaks at the angle $2\theta(°)$ ($\pm 0.2$) of 14.19, 17.33, 17.36, 20.31, 20.34, 20.54, 20.57, 20.61, 20.64, 20.67, 20.71, 20.74, 23.35, 23.42, 25.09, 25.12, 25.25, 25.29, 27.46, 27.53, 27.56, 28.73, 28.76, 33.14, 33.24, 33.27, 33.47, 33.54 and 42.26.

5. The crystalline dimethylamine salt of glyphosate according to the technical solution 4, characterized in that the X-ray powder diffraction pattern of this crystal further comprises one or more peaks at the angle $2\theta(°)$ ($\pm 0.2$) of 14.16, 14.32, 17.30, 17.40, 17.80, 17.83, 20.27, 21.04, 23.31, 23.45, 25.05, 26.42, 26.46, 27.43, 27.59, 28.70, 28.80, 30.40, 30.43, 30.47, 33.11, 33.31, 33.34, 33.38, 33.41, 33.44, 33.58, 33.61, 42.20, 42.36 and 51.22.

6. The crystal according to any of the technical solutions 1 to 5, characterized in that said crystal has the X-ray powder diffraction pattern as substantially shown in FIG. 1.

7. The crystal according to any of the technical solutions 1 to 6, characterized in that said crystal further has the infrared spectrum as substantially shown in FIG. 2 and/or a DSC thermal analysis results as substantially shown in FIG. 3.

8. A process for preparing the crystal according to any of the technical solutions 1 to 7, including the steps:

a) mixing glyphosate powders and an organic solvent under stirring to form a suspension;

b) introducing a dimethylamine gas into this mixture system to make it undergo a salt-formation reaction, wherein the mole number of the introduced dimethylamine gas is 1.0-3.0 times that of the glyphosate; the reaction temperature is controlled between 5 and 90° C.; and the reaction time is 1.5-5.0 h;

c) slowly decreasing the temperature to −5-50° C., with a slow stirring, and adding a crystal seed of dimethylamine salt of glyphosate, then resulting in crystals to start precipitating, slowly stirring further for 1.0-2.0 h till the precipitated crystals grow up, and then separating the crystals.

9. The process according to the technical solution 8, wherein the mole number of the dimethylamine gas is 1.0-2.5 times, preferably 1.1-1.4 times, that of the glyphosate.

10. The process according to the technical solution 8 or 9, wherein the reaction temperature is controlled between 5 and 40° C. and the reaction time is 2.0-4.0 h with a white suspending system being formed; the stirring speed is lowered and the temperature is slowly reduced to −5-20° C. and then the precipitated crystalline dimethylamine salt of glyphosate is separated.

11. The process according to the technical solution 10, wherein the reaction temperature is controlled between 25 and 40° C.; the reaction time is 2.5-3.0 h; and then the temperature is slowly reduced to 10-15° C.

12. The process according to the technical solution 8 or 9, wherein the reaction temperature is 40-90° C.; the reaction time is 1.0-3.0 h; and a clear solution of the dimethylamine salt of glyphosate is formed; then the stirring speed is lowered, the temperature is slowly reduced to −5-40° C., a crystal seed of dimethylamine salt glyphosate is added and further stirred for 1.0-2.0 h, and thereafter, the precipitated crystalline dimethylamine salt of glyphosate is separated.

13. The process according to the technical solution 12, wherein the reaction temperature is controlled between 50 and 70° C.; the reaction time is 1.5-2.0 h; and then the temperature is slowly reduced to 15-30° C.

14. A process for preparing a crystalline dimethylamine salt of glyphosate, including the steps:

a) introducing a portion of a dimethylamine gas into an organic solvent;

b) adding glyphosate powders under stirring and further introducing the remaining dimethylamine gas into the system, wherein the total mole number of the introduced dimethylamine gas is 1.0-1.4 times the mole number of the glyphosate; the reaction temperature is between 40 and 90° C.; and the reaction time is 1.5-2.5 h; and then obtaining a clear liquid system;

c) slowly lowering the temperature of the system to 15-25° C. and then adding a crystal seed of dimethylamine salt of glyphosate such that crystals are precipitated; and then separating the precipitated crystalline dimethylamine salt of glyphosate.

15. The process according to any of the technical solutions 8-14, wherein the organic solvent is selected from the group consisting of monohydric alcohol, dihydric alcohol and trihydric alcohol containing 1 to 6 carbon atoms; tetrahydrofuran, ethyl ether, petroleum ether; acetone, butanone; toluene, xylene, cyclohexane; dichloromethane; ethyl acetate; acetonitrile; DMSO; DMF; and mixtures thereof.

16. The process according to any of the technical solutions 8-14, wherein the organic solvent is selected from the group consisting of monohydric alcohol and dihydric alcohol containing 1 to 6 carbon atoms; petroleum ether; acetone; toluene, xylene, cyclohexane; dichloromethane; ethyl acetate; and mixtures thereof.

17. The process according to any of the technical solutions 8-14, wherein the organic solvent is selected from the group consisting of methanol, ethanol, ethylene glycol, propylene glycol, glycerol, cyclohexanol, petroleum ether, toluene, xylene, cyclohexane and mixtures thereof.

18. A process for preparing a crystalline dimethylamine salt of glyphosate, including the steps:
a) evenly mixing glyphosate with water and introducing into the mixture a dimethylamine gas with a mole number 1-1.5 times that of the glyphosate;
b) adding an organic solvent capable of being miscible or partially miscible with water to the reaction mixture after the completion of the reaction, and then separating the precipitated crystalline dimethylamine salt of glyphosate.

19. The process according to the technical solution 18, wherein the reaction temperature is between 5 and 90° C., preferably 30-70° C., and the weight ratio of the glyphosate to the water in the system is 0.2-4.0:1, preferably 1.0-2.5:1, and the weight ratio of the organic solvent as added to the water contained in the system is 1-10:1.

20. The process according to the technical solution 18 or 19, wherein the ability of said organic solvent to dissolve the dimethylamine salt of glyphosate is poorer than that of water to dissolve the dimethylamine salt of glyphosate, and said organic solvent is selected from the group consisting of methanol, ethanol, glycerol, butanol, cyclohexanol, acetone, toluene, xylene, ethyl ether, tetrahydrofuran, and mixtures thereof.

21. A solid herbicidal composition comprising the crystalline dimethylamine salt of glyphosate according to any of the technical solutions 1-7.

22. A solid herbicidal formulation comprising the crystalline dimethylamine salt of glyphosate according to any of the technical solutions 1-7 and an agriculturally acceptable carrier.

23. The formulation according to the technical solution 22, which is in the form of powders, granules or tablets.

24. The formulation according to the technical solution 22 or 23, wherein the carrier comprises an adjuvant and a filler.

25. The formulation according to the technical solution 24, wherein the adjuvant is selected from the group consisting of an alkylpolyglucoside, an aliphatic amine polyoxyethylene ether, a betaine type compound, sarcosine or a sarcosine salt, an aliphatic alcohol ethoxylate, a quaternary ammonium salt surfactant, an alkylamine, an alkylphenol polyoxyethylene ether, an organic silicon and the mixtures of two or more of said adjuvants; and/or
said filler is selected from the group consisting of a soluble inorganic salt, such as, ammonium sulfate, sodium sulfate, ammonium chloride and the like; kaolin; diatomite; attapulgite; clay; bentonites; argil; carbon-white; sepiolite; zeolite; talc; agalmatolite and the mixtures of two or more of said fillers.

26. The formulation according to any of the technical solutions 22-25, comprising by weight:

| | |
|---|---|
| crystalline dimethylamine salt of glyphosate | 20%-90% |
| adjuvant | 5%-30%, and |
| filler | 0%-75%, | based on the total weight of the formulation.

27. A method of controlling weeds or undesirable vegetation, which comprises applying the crystalline dimethylamine salt of glyphosate according to any of the technical solutions 1-7 dissolved by water or the herbicidal composition according to the technical solution 21 or the herbicidal formulation according to any of the technical solutions 22-26 to weeds or undesirable vegetation or the growth environment thereof.

Accordingly, on the one hand, the present invention provides the compound, a dimethylamine salt of N-phosphonomethyl glycine (i.e., dimethylamine salt of glyphosate) shown in formula (I), in crystalline form:

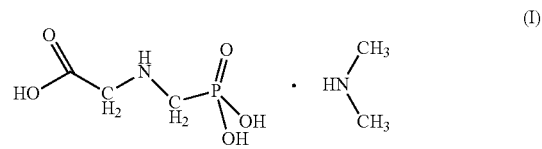

(I)

The X-ray powder diffraction pattern of this crystal has at least one or more, such as 2, 3, 4, 5 or 6, diffraction peaks with higher intensity at the angle 2θ(°) (±0.2) of 14.26, 20.44, 20.47, 25.19, 27.49 and 33.51.

In addition to the above diffraction peaks with higher intensity, the X-ray powder diffraction pattern of this crystal further comprises one or more diffraction peaks at the angle 2θ(°) (±0.2) of 14.22, 14.29, 20.37, 20.41, 20.51, 23.38, 25.15, 25.22, 33.17, 33.21 and 42.23.

In addition to the above diffraction peaks, the X-ray powder diffraction pattern of this crystal further comprises one or more peaks at the angle 2θ(°) (±0.2) of 14.19, 17.33, 17.36, 20.31, 20.34, 20.54, 20.57, 20.61, 20.64, 20.67, 20.71, 20.74, 23.35, 23.42, 25.09, 25.12, 25.25, 25.29, 27.46, 27.53, 27.56, 28.73, 28.76, 33.14, 33.24, 33.27, 33.47, 33.54 and 42.26.

In addition to the above diffraction peaks, the X-ray powder diffraction pattern of this crystal further comprises one or more peaks at the angle 2θ(°) (±0.2) of 14.16, 14.32, 17.30, 17.40, 17.80, 17.83, 20.27, 21.04, 23.31, 23.45, 25.05, 26.42, 26.46, 27.43, 27.59, 28.70, 28.80, 30.40, 30.43, 30.47, 33.11, 33.31, 33.34, 33.38, 33.41, 33.44, 33.58, 33.61, 42.20, 42.36 and 51.22.

The X-ray powder diffraction pattern of said crystalline dimethylamine salt of glyphosate is as substantially shown in FIG. 1.

In the present invention, the X-ray powder diffraction pattern of the crystalline dimethylamine salt of glyphosate as mentioned above is obtained by measurement with the known methods in the art using PANalytical X'Pert PRO X-ray diffractometer and Cu—Kα radiation (λ=0.1542 nm). Because of error of instrument or the difference in operator, a person skilled in the art would understand that the above parameter 2θ(°) for characterizing the crystal might have a slight difference.

The IR spectrum of the crystalline dimethylamine salt of glyphosate of the present invention is as substantially shown in FIG. 2. Said IR spectrum is measured by using Bruker TENSOR 27 in the mode of KBr tabletting.

By determination, the melting point of the crystalline dimethylamine salt of glyphosate of the present invention is 155.5-156.1° C. (the determination apparatus: BUCHI B545 melting point apparatus).

The DSC (Differential Scanning calorimeter) profile of the crystalline dimethylamine salt of glyphosate of the present invention is as substantially shown in FIG. 3. Determination apparatus: NETZSCH STA 449C; determination conditions: room temperature to 300° C., 3 K/min; atmosphere (purging gas): air, 50 ml/min; protection gas: Ar.

On the other hand, the present invention provides a production process of the crystalline dimethylamine salt of glyphosate, comprising:

adding glyphosate powders and a suitable amount of an organic solvent into a conventional reactor and mixing them under sufficient stirring, wherein the amount of the organic solvent added is not strictly limited and may be substantially the same as the weight of the glyphosate powders;

introducing a dimethylamine gas into this mixture to carry out the salt formation reaction, wherein the mole number of the introduced dimethylamine gas is 1.0-3.0 times, preferably 1.0-1.5 times, more preferably 1.1-1.4 times, that of the glyphosate, wherein the reaction temperature is controlled between 5 and 90° C., and the reaction time is 1.5-5 h;

lowering the stirring speed after the completion of the reaction, slowly reducing the temperature to −5-50° C., then adding a crystal seed of dimethylamine salt of glyphosate, and resulting in the crystalline dimethylamine salt of glyphosate to start precipitating;

performing the slow stirring further for 1.0-2.0 h till the precipitated crystals grow up, separating the dimethylamine salt of glyphosate by filter with suction, and then drying it to obtain the crystalline dimethylamine salt of glyphosate.

In one embodiment, in the process of the present invention, the reaction temperature is 5-40° C., preferably 25-40° C.; the reaction time is 2.0-4.0 h, preferably 2.5-3.0 h. After the completion of the reaction, a white suspending system is formed; the stirring speed is lowered; the temperature is slowly reduced to −5-20° C., preferably 10-15° C. After the further stirring of 1.5-2.0 h, the separation of the dimethylamine salt of glyphosate is carried out, as well as other subsequent operations. In this embodiment, since a small amount (about 5-10% of the weight concentration of the dimethylamine salt of glyphosate) of the dimethylamine salt of glyphosate produced from the reaction exists in crystalline form, this part of crystals will act as the crystal seed which starts the precipitation process of the crystalline dimethylamine salt of glyphosate.

In another embodiment of the present invention, the reaction temperature is controlled between 40 and 90° C., preferably 50-70° C.; the reaction time is 1.0-3.0 h, preferably 1.5-2.0 h. After the completion of the reaction, a clear solution of a dimethylamine salt of glyphosate is formed. Then, the stirring speed is lowered; the temperature is slowly reduced to −5-40° C., preferably 15-30° C. A crystal seed of dimethylamine salt of glyphosate is subsequently added. After the further stirring of 1.0-1.5 h, the separation of the dimethylamine salt of glyphosate is carried out, as well as other subsequent operations.

In the present invention, it is preferred to control the reaction temperature between 40 and 90° C., more preferably 50-70° C.

In the process of the present invention, the mother liquor from which the crystal is precipitated contains a solvent and a small amount of the dimethylamine salt of glyphosate. This mother liquor can be returned to serve as the solvent for the next batch of reaction. Meanwhile, a suitable amount of the organic solvent is supplemented to supply the deficiency in solvent owing to the partial loss in mother liquor. The mother liquor can be directly recycled for use, for example, recycled around 6 to 15 batches. After the last batch of mother liquor is distilled or rectified to recover the solvent, the residual liquor may be used for formulating an aqueous formulation of the dimethylamine salt of glyphosate, such as an aqueous formulation containing 35% dimethylamine salt of glyphosate.

In another embodiment, the process of the present invention comprises the following steps: firstly, introducing a portion of a dimethylamine gas into an organic solvent, then adding glyphosate powders, stirring them, further introducing the left dimethylamine gas into the system with the total mole number of the introduced dimethylamine gas being 1.0-1.4 times the mole number of the glyphosate powders and the reaction temperature being 40-90° C.; proceeding the reaction for 1.5-2.5 h, thereby a clear liquid system being formed; then slowly reducing the temperature to 15-25° C., adding a crystal seed of dimethylamine salt of glyphosate, and further slowly stirring the system for 1-1.5 h after the precipitation of crystals to thoroughly precipitate the crystals, and finally separating the crystalline dimethylamine salt of glyphosate by filtration.

The organic solvent in the above process of the present invention is selected from the group consisting of alcohols, ethers, ketones, esters, amides, nitriles, aromatic hydrocarbons, alkanes, haloalkanes and mixtures thereof; preferably monohydric alcohol, dihydric alcohol and trihydric alcohol containing 1 to 6 carbon atoms, in particular, e.g., methanol, ethanol, ethylene glycol, propylene glycol, glycerol, cydohexanol; tetrahydrofuran, ethyl ether, petroleum ether; acetone, butanone; toluene, xylene, cyclohexane; dichloromethane; ethyl acetate; acetonitrile; DMSO; DMF; and mixtures thereof; in particular, methanol, ethanol, ethylene glycol, propylene glycol, glycerol, cyclohexanol, petroleum ether, toluene, xylene or cyclohexane and mixtures thereof; particularly preferably, ethylene glycol, propylene glycol, glycerol, cyclohexanol, ethanol, methanol, toluene, xylene and mixtures thereof.

In one embodiment, when the organic solvent is preferably propylene glycol, glyphosate powders and a suitable amount of propylene glycol are mixed under sufficient stirring. Then, a dimethylamine gas is introduced into the mixture for reaction, wherein the mole number of the introduced dimethylamine gas is 1.0-1.4 times that of the glyphosate powders; the reaction temperature is controlled between 25 and 75° C., preferably 50-75° C.; the reaction time is 1.5-5.0 h, preferably 1.5-2.5 h. After the completion of the reaction, the stirring speed is lowered; the temperature is slowly reduced to −5-30° C., preferably 15-25° C. Then, a crystal seed of dimethylamine salt of glyphosate is added. And the crystalline dimethylamine salt of glyphosate starts to be precipitated. The slow stirring is further performed for 1.0-2.0 h till the crystals grow up. Then, the crystalline dimethylamine salt of glyphosate is separated by filter with suction.

Further, the present invention provides another production process of a crystalline dimethylamine salt of glyphosate, comprising the following steps: firstly, adding a suitable amount of water into a reaction kettle and adding under stirring, once or in batches, glyphosate powders with the weight which is 0.2-4.0 times, preferably 0.5-3.0 times, more preferably 1.0-2.5 times, that of the water; introducing into the reaction kettle a dimethylamine gas with a mole number which is 1-1.5 times that of the glyphosate and controlling the reaction temperature between 5 and 90° C., preferably 30-80° C., more preferably 30-50° C.; adding into the reaction mixture an organic solvent capable of being miscible or partially miscible with water which has the amount (volume) 1-10 times that of the water after the proceeding of reaction for 1.0-3.0 h, preferably 1.5-2.0 h; cooling the temperature to 15-50° C., preferably 15-35° C., under a slow stirring; and separating by filtering with suction or centrifugalizing the crystalline dimethylamine salt of glyphosate precipitated from crystallization.

Since the aqueous solution of high concentration dimethylamine salt of glyphosate has a relatively great viscosity, if the temperature is reduced immediately after the completion of reaction, the viscosity will increase suddenly so there is no need to reduce temperature after the completion of the reaction, and the organic solvent is directly added. The crystalline dimethylamine salt of glyphosate will be precipitated in the meantime of temperature being lowered by the dilution.

As for the organic solvent capable of being miscible or partially miscible with water in this process, its ability to dissolve a dimethylamine salt of glyphosate should be poorer than that of water to dissolve a dimethylamine salt of glyphosate, and it includes methanol, ethanol, glycerol, acetone, cyclohexanol, butanol, toluene, xylene, ethyl ether, tetrahydrofuran and the like, and mixtures thereof.

Since the reactivity of glyphosate with a dimethylamine gas in water is higher than that of glyphosate with an ammonia gas in water and the solubility of the generated dimethylamine salt of glyphosate in water is also greater than that of ammonium glyphosate in water, in comparison with the ammonium salt-forming reaction, the synthetic conditions of dimethylamine salt of glyphosate in the present process are milder relatively; meanwhile, the water amount required in the reaction system is less, thereby the amount of organic solvent as required is also less.

In addition, a small amount of an organic solvent may be also used to extract out partial water from the mother liquor system from which the crystalline dimethylamine salt of glyphosate is separated, and then a surfactant is directly added into the mother liquor to produce an aqueous formulation with a high content of the dimethylamine salt of glyphosate, e.g., an aqueous formulation containing 35% dimethylamine salt of glyphosate. The technique is simple with low cost.

When this process is used, since the dimethylamine salt of glyphosate produced in reaction is soluble or mostly soluble in the reaction system, the reaction time is short, and the reaction is completed thoroughly, and has a high yield. Also, the crystalline dimethylamine salt of glyphosate produced by this process is a white crystalline powder which can flow freely and has homogenous particle size.

The present invention further provides a solid herbicidal composition and formulation comprising the crystalline dimethylamine salt of glyphosate. In the solid herbicidal formulation of the present invention, an agriculturally acceptable carrier is further comprised in addition to the crystalline dimethylamine salt of glyphosate. Said carrier includes adjuvants and fillers etc, as well as other common carriers applicable to herbicidal formulations.

The present invention also provides a process for the preparation of the solid formulation of dimethylamine salt of glyphosate: certain amounts of the crystalline dimethylamine salt of glyphosate, an adjuvant and a filler are evenly mixed, and are then subjected to one or more steps of pulverization, granulation and drying to obtain the solid formulation of dimethylamine salt of glyphosate.

In the solid formulation of dimethylamine salt of glyphosate provided in the present invention, the various components, based on the total weight of the formulation, have the following specific proportions:

| | |
|---|---|
| dimethylamine salt of glyphosate | 20%-90% |
| adjuvant | 5%-30%, and |
| filler | 0%-75%. |

The solid formulation of dimethylamine salt of glyphosate in the present invention includes powders, granules, tablets and so on. The powder formulation can be directly obtained by, for example, mixing and pulverizing the various components; the granule formulation can be obtained by mixing, pulverizing, granulating and drying all components; the tablet formulation can be obtained by mixing, pulverizing and tabletting all components.

The adjuvant in the solid formulation of dimethylamine salt of glyphosate in the present invention is selected from the group consisting of an alkylpolyglucoside, an aliphatic amine polyoxyethylene ether, a betaine type compound, sarcosine or a sarcosine salt, an aliphatic alcohol ethoxylate, an quaternary ammonium salt surfactant, an alkylamine, an alkylphenol polyoxyethylene ether, an organic silicon adjuvant and the mixtures of two or more of said adjuvants; and other common adjuvants applicable to herbicidal formulations; preferably, an alkylpolyglucoside and an aliphatic amine polyoxyethylene ether.

The filler in the solid formulation of dimethylamine salt of glyphosate in the present invention may use a soluble inorganic salt, such as, ammonium sulfate, sodium sulfate, ammonium chloride and the like; kaolin; diatomite; attapulgite; clay; bentonites; argil; carbon-white; sepiolite; zeolite; talc; agalmatolite and the like, and the mixtures of two or more of said fillers; preferably, ammonium sulfate.

In the present invention, said alkylpolyglucoside has the following formula:

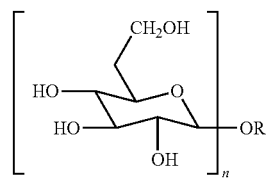

wherein R is preferably a $C_6$-$C_8$, more preferably, a $C_8$-$C_{12}$ straight or branched chain, saturated or unsaturated hydrocarbon, n is 1-8, for example, but not limited to, APG0810, APG1214, APG0814, APG0816, APG1216 and so on.

In the present invention, said aliphatic amine polyoxyethylene ether has the following formula:

  (I)

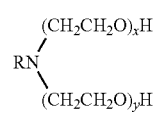  (II)

wherein R is preferably a $C_8$-$C_{22}$, more preferably, a $C_{12}$-$C_{18}$ straight or branched chain, saturated or unsaturated hydrocarbon; x+y is 0-40, preferably 2-30; n is 2-10. It is, for example, but not limited to, tallow amine polyoxyethylene ether, octadecylamine polyoxyethylene ether, rosin amine polyoxyethylene ether, coco amine polyoxyethylene ether, dodecyl amine polyoxyethylene ether, octadecyl amine polyoxyethylene ether, tallow amine polyoxyethylene ether and so on.

In the present invention, the adjuvant betaine type compound has the following formula:

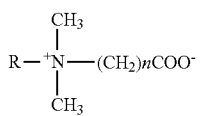

wherein R is $C_2$-$C_{22}$; n is 1 or 2. It is, preferably, cocamidopropyl betaine, dodecyl dimethyl betaine and so on.

In the present invention, said sarcosine and sarcosine salt have the following formula:

wherein X is hydrogen ion or metallic cation or other cationic groups, and may be selected from, for example, sodium cation, cations formed from amine such as octadecylamine cation and so on.

In the present invention, said aliphatic alcohol ethoxylate has the following formula:

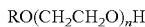

wherein R is a $C_1$-$C_{15}$, preferably, a $C_1$-$C_{12}$ straight or branched, saturated or unsaturated hydrocarbon; n is 2-10. It is, for example, but not limited to, lauryl alcohol polyoxyethylene ether or $C_1$-$C_{12}$ aliphatic alcohol polyoxyethylene polyoxypropylene ether.

In the present invention, said quaternary ammonium salt surfactant has the following formula:

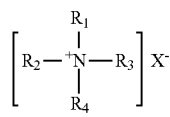

wherein $X^-$ represents halide ions, preferably, chloride; $R_1$, $R_2$, $R_3$ and $R_4$ may be same or different, being a $C_1$-$C_{18}$, preferably $C_1$-$C_{12}$, a linear or branched chain, saturated or unsaturated hydrocarbon. It is, for example, but not limited to, dodecyltrimethylammonium chloride, dodecyldimethylbenzylammonium chloride, octadecyldimethylhydroxyethylammonium nitrate, octadecyldimethylhydroxyethylammonium perchloride, octadecyldimethylhydroxyethyl laurate, octadecamideethyldiethylbenzylammoninum chloride, Arquad 2C-75® (AkzoNobel company) and so on.

In the present invention, said alkylamine has the following formula:

wherein $R_1$ is a $C_8$-$C_{24}$, preferably, a $C_{12}$-$C_{18}$ straight or branched chain, saturated or unsaturated hydrocarbon; $R_2$ and $R_3$, each independently, represent $C_1$-$C_4$, preferably, $C_1$-$C_2$ alkyl. It is, for example, but not limited to, dodecylamine, octadecylamine, dioctadecylamine, trialkylamine and so on.

In the present invention, said alkylphenol polyoxyethylene ether has the following formula:

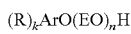

wherein R is a $C_4$-$C_{13}$ straight or branched alkyl; k is 1, 2 or 3; n is EO (ethylene oxide unit) addition mole number, generally 3-100. It is, for example, but not limited to, NP (nonylphenol polyoxyethylene ether) or OP series (octylphenol polyoxyethylene ether) and so on.

In the present invention, said organic silicon adjuvant has the following formula:

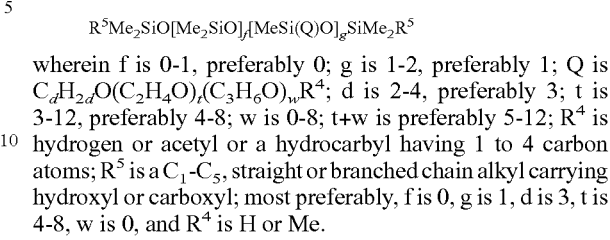

wherein f is 0-1, preferably 0; g is 1-2, preferably 1; Q is $C_dH_{2d}O(C_2H_4O)_t(C_3H_6O)_wR^4$; d is 2-4, preferably 3; t is 3-12, preferably 4-8; w is 0-8; t+w is preferably 5-12; $R^4$ is hydrogen or acetyl or a hydrocarbyl having 1 to 4 carbon atoms; $R^5$ is a $C_1$-$C_5$, straight or branched chain alkyl carrying hydroxyl or carboxyl; most preferably, f is 0, g is 1, d is 3, t is 4-8, w is 0, and $R^4$ is H or Me.

The process for the preparation of the crystalline dimethylamine salt of glyphosate in the present invention possesses simple techniques. As compared to the technique for preparing the ammonium salt of glyphosate, the operating conditions of the preparation process of the present invention are more mild with less organic solvent required. The process of the present invention has a high yield, above 97%, higher than that of the preparation techniques of other salts, such as an ammonium salt, of glyphosate.

The solubility in water of the crystalline dimethylamine salt of glyphosate prepared by the process of the present invention significantly increases as compared to that of the ammonium glyphosate and the like so that the formulation product with a high content of dimethylamine salt of glyphosate may be produced; the processing techniques are simplified; and the cost is reduced. The solid herbicidal formulation produced from the crystalline dimethylamine salt of glyphosate of the present invention has a high content of the active ingredient glyphosate. Therefore, the costs of production, packaging, storage and transport of the product are reduced to a large extent. As compared to an aqueous formulation, the crystalline dimethylamine salt of glyphosate itself, and the solid formulation of the dimethylamine salt of glyphosate with a high content of glyphosate in the present invention are more convenient to use and carry and will be labor-saving. In addition, it has been proven by experiments that the crystalline dimethylamine salt of glyphosate itself, and the solid formulation of the dimethylamine salt of glyphosate with a high content of glyphosate in the present invention have the herbicidal efficiency higher than that of an aqueous formulation product.

EMBODIMENTS

Figure 1:
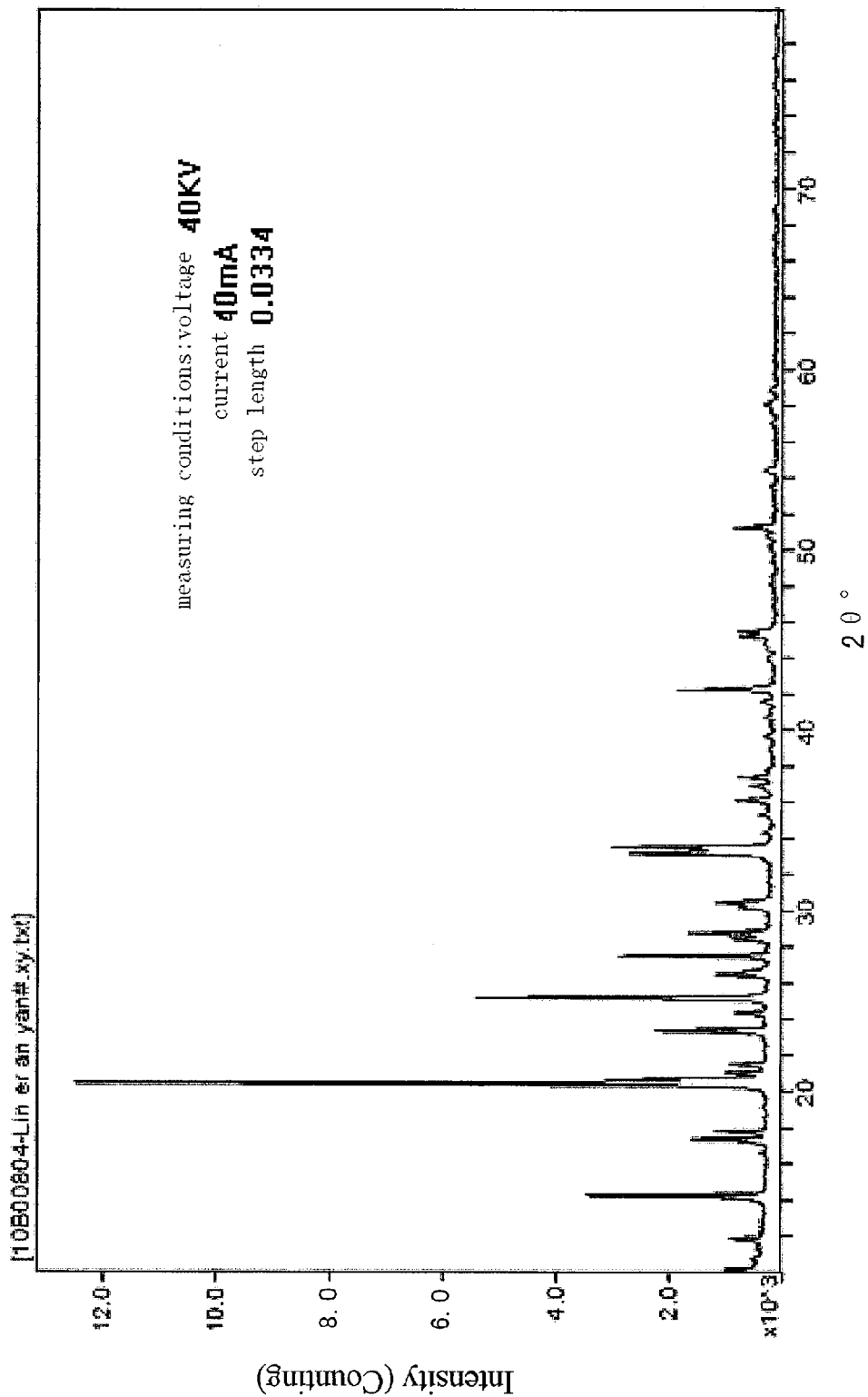
FIG. 1 is the X-ray powder diffraction pattern of the crystalline dimethylamine salt of N-phosphonomethyl glycine (dimethylamine salt of glyphosate) of the present invention.

The present invention is further described with the following examples. It should be understood that these examples are only intended to illustrate the present invention, not to limit the scope thereof.

The major starting material for reaction used in the examples, glyphosate, is the product of Zhejiang Wynca Chemical Industry Group Co., Ltd (batch number: 2009070301; purity: 95%). The dimethylamine gas is the product of Quzhou Jiangshan Chemical Industry Plant, with a purity of 99.5%. Other substances used in the examples without specific sources as indicated are all commercially available industrially pure or analytically pure graded merchandise. The experimental conditions without specific indication are conventional conditions or the conditions advised by the manufacturers. Unless otherwise indicated, the parts and percentages in the examples all refer to the weight parts and weight percentages.

Preparation of Crystalline Dimethylamine Salt of Glyphosate

Example 1

Into a 500 mL round-bottomed flask equipped with a stirring apparatus, thermometer, a condensing apparatus and a water bath for cooling, 150 g cyclohexanol was added, and 150 g of a dry powder of glyphosate (manufactured by Zhejiang Wynca Chemical Industry Group Co., Ltd, batch number: 2009070301; purity: 95%) was added under stirring. The mixture presented in a suspension system. A dimethylamine gas (purchased from Quzhou Jiangshan Chemical Industry Plant, with a purity of 99.5%) in a mole number of 1.1 times that of the glyphosate was introduced into the system which was then cooled with the water bath to control the reaction temperature at 50-55° C. After the reaction lasted for 1.5-2.5 h, the system became clear. Under stirring, the temperature was slowly reduced to 20-30° C. A crystal seed of dimethylamine salt of glyphosate was added. The slow stirring continued for 1-1.5 h after the crystals were precipitated. The crystals were then filtered and dried to give a 172.6 g crystalline dimethylamine salt of glyphosate, while the content of the dimethylamine salt of glyphosate was 95.9% (based on the dimethylamine salt of glyphosate) by analysis. The filtered mother liquor could be recycled as a solvent.

1H-NMR (BRUKER AVANCE, 500 MHz, $D_2O$): δ3.6 (2H, s), 3.07 (2H, d), 2.57 (2H, s).

MS: ESI (Thermo LCQ DECA XP MAX ion trap mass spectrometer, +ESI, 4.5 KV; −ESI: −3.5 KV): 214.9

Example 2

Into a 500 mL round-bottomed flask equipped with a stirring apparatus, thermometer, a condensing apparatus and a water bath for cooling, 150 g ethylene glycol was added, and 163 g wet glyphosate (the dry matter purity: 95%; moisture content: 8%; manufactured by Zhejiang Wynca Chemical Industry Group Co., Ltd, batch number: 2009070301) was added under stirring. The mixture presented in a suspension system. A dimethylamine gas in a mole number 1.2 times that of the glyphosate was introduced into the system which was then cooled with the water bath to control the reaction temperature at 30-55° C. After the reaction lasted for 1.5-2.5 h, the system became clear. Then, the temperature was slowly reduced to 0-15° C. A crystal seed of dimethylamine salt of glyphosate was added. The slow stirring continued for 1-1.5 h after the crystals were precipitated. The crystals were then filtered and dried to give a 160.2 g crystalline dimethylamine salt of glyphosate, while the content of the dimethylamine salt of glyphosate was 96.3% (based on the dimethylamine salt of glyphosate) by analysis. The filtered mother liquor could be recycled as a solvent, or was distilled (rectified) to recover ethylene glycol and was then used for formulating an aqueous formulation containing 35% dimethylamine salt of glyphosate.

Example 3

Into a 10 L reaction kettle equipped with a stirring apparatus, thermometer, a condensing apparatus and a jacket for cooling, 3000 g glycerol was added, and 3000 g dry powder of glyphosate (purity: 95%) was added under stirring. The mixture presented in a suspension system. A dimethylamine gas in a mole number 1.2 times that of the glyphosate was introduced into the system which was then cooled with the jacket to control the reaction temperature at 15-35° C. After the reaction lasted for 2.0-4.0 h, the mixture presented in a white suspension system. Then, the temperature was reduced to −5-10° C. The system was slowly stirred for 1-1.5 h, and was then filtered and the filtered cake was dried to give a 3425.8 g crystalline dimethylamine salt of glyphosate, while the content of the dimethylamine salt of glyphosate was 96.0% (based on the dimethylamine salt of glyphosate) by analysis. The filtered mother liquor could be recycled as a solvent, or was distilled (rectified) to recover glycerol and was then used for formulating an aqueous formulation containing 35% dimethylamine salt of glyphosate.

Example 4

Into a 10 L reactor equipped with a stirring apparatus, thermometer, a condensing apparatus and a jacket for cooling, 3000 g toluene was added, and 3000 g dry powder of glyphosate (purity: 95%) was added under stirring. The mixture presented in a suspension system. A dimethylamine gas in a mole number 1.1 times that of the glyphosate was introduced into the system which was then cooled with the jacket to control the reaction temperature at 50-70° C. After the reaction lasted for 1.5-3.0 h, the system became clear. Then, the temperature was reduced to 10-25° C. The system was slowly stirred for 1-1.5 h, and was then filtered and the filtered cake was dried to give a 3380.3 g crystalline dimethylamine salt of glyphosate, while the content of the dimethylamine salt of glyphosate was 96.2% (based on the dimethylamine salt of glyphosate) by analysis. The filtered mother liquor could be recycled as solvent, or was distilled (rectified) to recover toluene and was then used for formulating an aqueous formulation containing 35% dimethylamine salt of glyphosate.

Example 5

Into a 3000 L reactor kettle equipped with a stirring apparatus, thermometer, a, jacket for cooling and a tail gas condensing apparatus, 900 kg toluene was added, and 900 kg dry powder of glyphosate (purity: 95%) was added under stirring. The mixture presented in a suspension system. A dimethylamine in a mole number 1.2 times that of the glyphosate was added dropwise into the reaction kettle in a manner of keeping the dimethylamine storage tank at low temperature (about 3° C. or below) and pressing nitrogen into the tank to discharge the dimethylamine liquid. The jacket was used for cooling to control the reaction temperature at 10-40° C. After the reaction lasted for 2.0-4.0 h, the mixture presented in a white suspension system. Then, the temperature was reduced to 0-20° C. The system was slowly stirred for 1.0-2.0 h, and was then filtered and the filtered cake was dried to give a 1030.1 kg crystalline dimethylamine salt of glyphosate, while the content of the dimethylamine salt of glyphosate was 96.5% (based on the dimethylamine salt of glyphosate) by analysis. The filtered mother liquor could be recycled as solvent, or was distilled (rectified) to recover toluene and was then used for formulating an aqueous formulation containing 35% dimethylamine salt of glyphosate.

Example 6

Into a 500 mL reactor equipped with a stirring apparatus, thermometer, a condensing apparatus and a water bath for cooling, 50 g water was added, and 100 g dry powder of glyphosate (glyphosate content: 95%) was added in batches under stirring. A 30.4 g dimethylamine gas was introduced. The reaction temperature was controlled by water bath at 40-70° C., and the reaction lasted for 1.5 h. After the completion of reaction, 300 g toluene was added. The mixture was slowly stirred and cooled to 20° C., and was then filtered with suction and the filtered cake was dried to give a 108.2 g crystalline dimethylamine salt of glyphosate, while the content of the dimethylamine salt of glyphosate was 96.0% (based on the dimethylamine salt of glyphosate) by analysis.

Example 7

The experimental steps and apparatuses were the same as Example 1, but industrial ethanol replaced cyclohexanol as a solvent to give a crystalline dimethylamine salt of glyphosate.

Example 8

The experimental steps and apparatuses were the same as Example 1, but methanol replaces cyclohexanol as solvent to give out the crystalline dimethylamine salt of glyphosate.

Example 9

The experimental steps and apparatuses were the same as Example 1, but xylene replaced cyclohexanol as a solvent to give the crystalline dimethylamine salt of glyphosate.

Example 10

The experimental steps and apparatuses were the same as Example 1, but cyclohexane replaced cyclohexanol as a solvent to give the crystalline dimethylamine salt of glyphosate.

Example 11

Based on Examples 1-9 respectively, the recovered mother liquor was returned for use as the solvent to carry out the next batch of reaction.

Example 12

The experimental steps and apparatuses were the same as Example 10. The mother liquor was returned for recycling use not less than 5 times. Upon each use, a suitable amount of the solvent cyclohexane was supplemented till the sum of the practical amounts of adding solvent and mother liquor was identical to the amount of adding solvent in Example 10.

Example 13

Into a 500 mL reactor equipped with a stirring apparatus, thermometer, a condensing apparatus and a water bath for cooling, 150 g ethylene glycol was added, and a 20 g dimethylamine gas was introduced, which then paused. 150 g dry powder of glyphosate (purity: 95%) was added under stirring. The mixture presented in a suspension system. Then the left dimethylamine gas (the total dimethylamine gas had a mole number 1.2 times that of the glyphosate) was introduced into the system which was then cooled with the water bath to control the reaction temperature at 40-55° C. After the reaction lasted for 1.5-2.5 h, the system became clear. Then, the temperature was slowly reduced to 25° C. A crystal seed of dimethylamine salt of glyphosate was added. The slow stirring continued for 1-1.5 h after the crystals were precipitated. The crystals were then filtered and dried to give a 174.6 g crystalline dimethylamine salt of glyphosate, while the content of the dimethylamine salt of glyphosate was 95.3% (based on the dimethylamine salt of glyphosate) by analysis. The filtered mother liquor could be recycled as a solvent, or was distilled (rectified) to recover ethylene glycol and was then used for formulating an aqueous formulation containing 35% dimethylamine salt of glyphosate.

The following table provided the purity (weight percentage) and yield of the products in examples. The yield was calculated by glyphosate (purity: 95%).

| Example | Dimethylamine salt of glyphosate (%) | Yield (%) |
| --- | --- | --- |
| 1 | 95.9 | 98.7 |
| 2 | 96.3 | 99.0 |
| 3 | 96.0 | 98.8 |
| 4 | 96.2 | 99.3 |
| 5 | 96.5 | 99.1 |
| 6 | 96.0 | 98.8 |
| 7 | 95.3 | 99.0 |
| 8 | 95.1 | 98.8 |
| 9 | 95.5 | 97.9 |
| 10 | 95.8 | 98.8 |
| 13 | 95.3 | 99.1 |

Preparation of a Solid Formulation of Dimethylamine Salt of Glyphosate

Example 14

Preparation of a Soluble Granule Containing 20% Dimethylamine Salt of Glyphosate To 23.1 g wet crystalline powder of the dimethylamine salt of glyphosate (drying loss: 9%; the dimethylamine salt of glyphosate in dry powder had a content of 95.3%) produced in any of the abovementioned Examples 1-12, 66.9 g ammonium sulfate as a filler and 10 g alkylpolyglucoside (trade name: APG0810, manufactured by Nanjing Jinling Petrochemical Research Institute Co., Ltd.) as an adjuvant were added. The resultant was evenly stirred and then granulated and dried to produce a soluble granule containing 20% dimethylamine salt of glyphosate.

Example 15

Preparation of a Soluble Powder Containing 50% Dimethylamine Salt of Glyphosate

To 52.5 g crystalline powder of the dimethylamine salt of glyphosate (the content of the dimethylamine salt of glyphosate: 95.3%) produced in any of the abovementioned Examples 1-12 and treated by drying, 42.5 g sodium sulfate as a filler and 5 g aliphatic amine polyoxyethylene ether (trade name: 267e, manufactured by Clariant Chemicals (China) Ltd.) as an adjuvant were added. The resultant was evenly mixed and then dried and pulverized to produce a soluble powder containing 50% dimethylamine salt of glyphosate.

Example 16

Preparation of a Tablet Containing 70% Dimethylamine Salt of Glyphosate

To 73.5 g crystalline powder of the dimethylamine salt of glyphosate (the content of the dimethylamine salt of glyphosate: 95.3%) produced in any of the abovementioned Examples 1-12 and treated by drying, the filler ammonium sulfate 6.5 g and adjuvant betaine (trade name: CAB-30, purchased from Zhejiang Zanyu Technology Co., Ltd.) 20 g were added. The resultant was evenly mixed and then tableted to produce a tablet containing 70% dimethylamine salt of glyphosate.

Example 17

Preparation of a Granule Containing 80% Dimethylamine Salt of Glyphosate

To 83.9 g crystalline powder of the dimethylamine salt of glyphosate (the content of the dimethylamine salt of glyphosate: 95.3%) produced in any of the abovementioned Examples 1-12 and treated by drying, 1.1 g diatomite as a filler and 15 g sodium sarcosine (trade name: Empigen RSL/A, manufactured by Albright & Wilson Co., Ltd.) as an adjuvant were added. The resultant was evenly mixed by stirring and then granulated and dried to produce a granule containing 80% dimethylamine salt of glyphosate.

Example 18

Preparation of a Powder Containing 40% Dimethylamine Salt of Glyphosate

To 42.0 g crystalline powder of the dimethylamine salt of glyphosate (the content of the dimethylamine salt of glyphosate: 95.3%) produced in any of the abovementioned Examples 1-12 and treated by drying, 43 g Kaolin as a filler, 10 g aliphatic amine polyoxyethylene ether (trade name: 267e, manufactured by Clariant Chemicals (China) Ltd.) and 5 g alkylployglucoside (trade name: APG0810, manufactured by Nanjing Jinling Petrochemical Research Institute Co., Ltd.) as adjuvants were added. The resultant was evenly mixed by stirring and then dried and pulverized to produce a powder containing 40% dimethylamine salt of glyphosate.

Assay on the Herbicidal Efficacy of the Crystalline Dimethylamine Salt of Glyphosate and its Formulation Example 19

Assay on Herbicidal Efficacy

The inventor conducted the field potency comparative test for the crystalline dimethylamine salt of glyphosate and the solid formulation comprising crystalline dimethylamine salt of glyphosate produced by the process of the present invention, and the commercially available aqueous formulation comprising a dimethylamine salt of glyphosate.

A sample was taken in an effective ingredient amount of 60 g/mou (based on glyphosate), and was diluted by water to 30 l/mou. The resulting diluted liquor was evenly sprayed into a test field plot with an area of 2 m×2.5 m, repeated twice. Weeds for test included the annual weeds: Common Crabgrass (*Digitaria sanguinalis* (Linn.) Scop., Goosegrass (Wiregrass, *Eleusine indica* (Linn.) Gaertn., and Bitter Fleabane (Erigeron acer Linn.), and perennial weeds: Alligator Alternanthera Herb (*Alternanthera philoxeroides* (Mart.) Griseb), which weeds were in a prosperous growth period. On the day of application, it was a sunny day with the highest temperature of 37° C. After application, the days were mainly sunny or had shower at times with the temperature ranging between 25.3° C. and 36.2° C. At 2.5, 5, 7 and 11 days after application, the test weeds were observed for their subsistence. A CD Observation Method was used to make records. The test results were shown in Table 1.

Assessment Criteria of the CD Observation Method

A visual method was used with the following criteria:
2.0 mild poisoning symptom in a spot of leaves
4.0 a few leaves lost green or turned yellow while the plant growth was substantially normal
6.0 leaves lost green or turned yellow or some leaves withered, while the stalk was nearly normal, and was yet able to grow slowly
8.0 caulicle or inflorescence and rachis of leaves withered; most of stalk turned yellow or lost green mildly and was unable to grow normally; the plant died locally
10.0 the whole plant died

TABLE 1

Comparative Test on the Efficacy between crystalline dimethylamine salt of glyphosate, its formulation and commercially available aqueous formulation

| Sample name | Effective ingredient (glyphosate g/mou) | Days for weeds to die (d) | Control on annual weeds | Control on perennial weeds |
|---|---|---|---|---|
| commercially available aqueous formulation of dimethylamine salt of glyphosate (630 g/L, Tradename: Duramax, DOW AGROSCIENCES LLC) | 60 | 10~12 | 9.4 | 9.2 |
| crystalline dimethylamine salt of glyphosate | 60 | 9~11 | 9.6 | 9.4 |
| A granule containing 80% dimethylamine salt of glyphosate | 60 | 9~11 | 9.7 | 9.5 |

The test showed that the herbicidal efficacy of the crystalline dimethylamine salt of glyphosate itself and the solid formulation containing the crystalline dimethylamine salt of glyphosate as obtained by the process of the present invention both achieved or even exceeded the commercially available aqueous formulation comprising a dimethylamine salt of glyphosate.

Although the embodiments of the present invention have been described and explained in detail in the text above, it should be stated that a person skilled in the art may follow the contents disclosed in the present application to make a lot of changes or modifications to the above embodiments without violating the spirit and scope of the present invention, yet these variations should be all within the scope as disclosed in the claims.

The invention claimed is:
1. Crystalline dimethylamine salt of N-phosphonomethyl glycine (glyphosate) shown in formula (I):

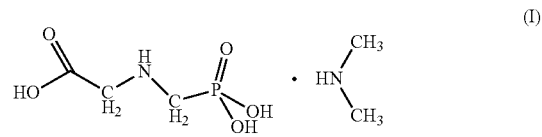

wherein the X-ray powder diffraction pattern of this crystal has at least one or more peaks at the angle 2θ(°) (±0.2) of 14.26, 20.44, 20.47, 25.19, 27.49 and 33.51.

2. The crystalline dimethylamine salt of glyphosate according to claim 1, wherein the X-ray powder diffraction pattern of this crystal has peaks at the angle 2θ(°) (±0.2) of 14.26, 20.44, 20.47, 25.19, 27.49 and 33.51.

3. The crystalline dimethylamine salt of glyphosate according to claim 1, wherein the X-ray powder diffraction pattern of this crystal further comprises one or more peaks at the angle 2θ(°) (±0.2) of 14.22, 14.29, 20.37, 20.41, 20.51, 23.38, 25.15, 25.22, 33.17, 33.21 and 42.23.

4. The crystalline dimethylamine salt of glyphosate according to claim 3, wherein the X-ray powder diffraction pattern of this crystal further comprises one or more peaks at the angle 2θ(°) (±0.2) of 14.19, 17.33, 17.36, 20.31, 20.34, 20.54, 20.57, 20.61, 20.64, 20.67, 20.71, 20.74, 23.35, 23.42, 25.09, 25.12, 25.25, 25.29, 27.46, 27.53, 27.56, 28.73, 28.76, 33.14, 33.24, 33.27, 33.47, 33.54 and 42.26.

5. The crystalline dimethylamine salt of glyphosate according to claim 4, wherein the X-ray powder diffraction pattern of this crystal further comprises one or more peaks at the angle 2θ(°) (±0.2) of 14.16, 14.32, 17.30, 17.40, 17.80, 17.83, 20.27, 21.04, 23.31, 23.45, 25.05, 26.42, 26.46, 27.43, 27.59, 28.70, 28.80, 30.40, 30.43, 30.47, 33.11, 33.31, 33.34, 33.38, 33.41, 33.44, 33.58, 33.61, 42.20, 42.36 and 51.22.

6. The crystal according to claim 1, wherein said crystal has the X-ray powder diffraction pattern as substantially shown in FIG. 1.

Figure 2:
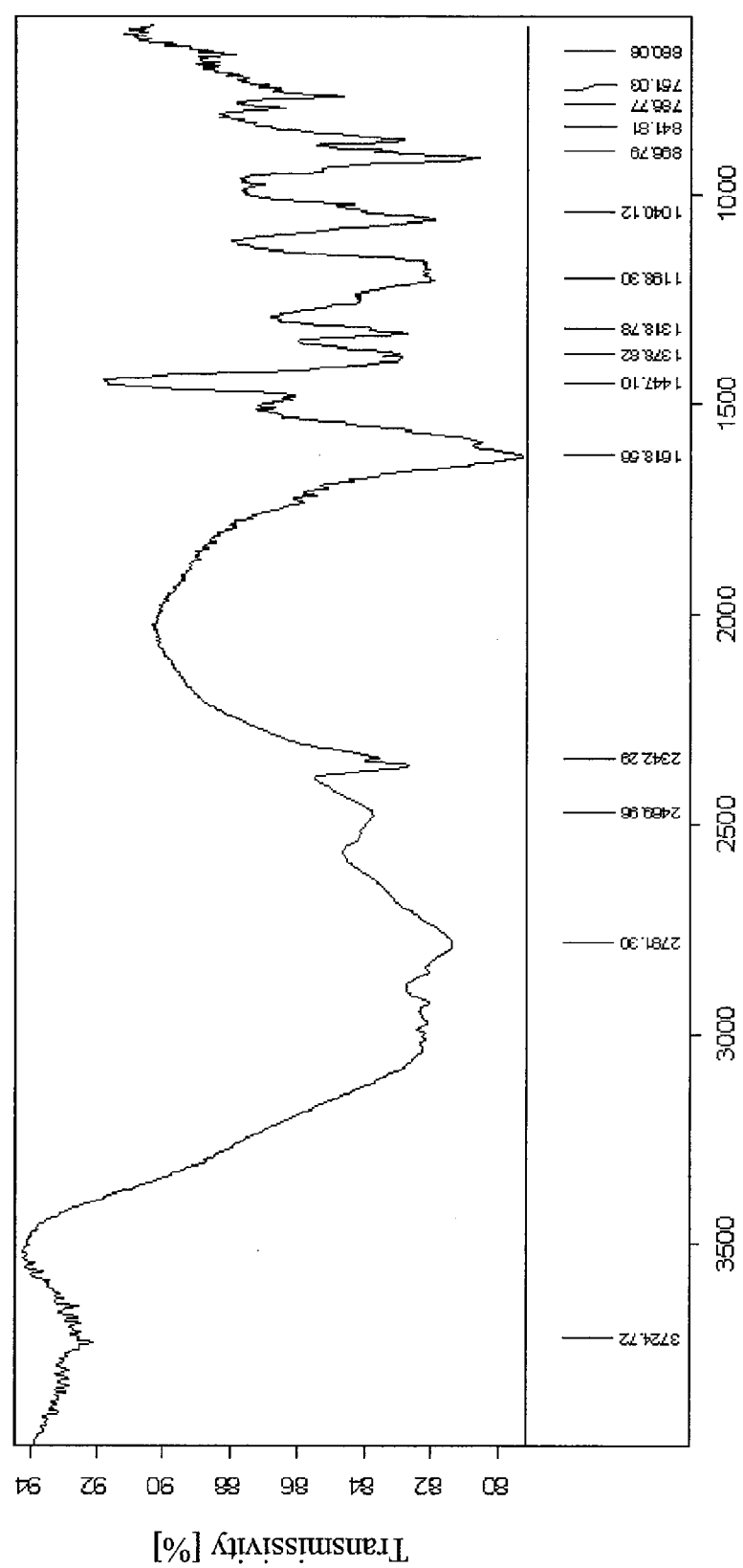
FIG. 2 is the IR spectrum of the crystalline dimethylamine salt of glyphosate of the present invention.
Figure 3:
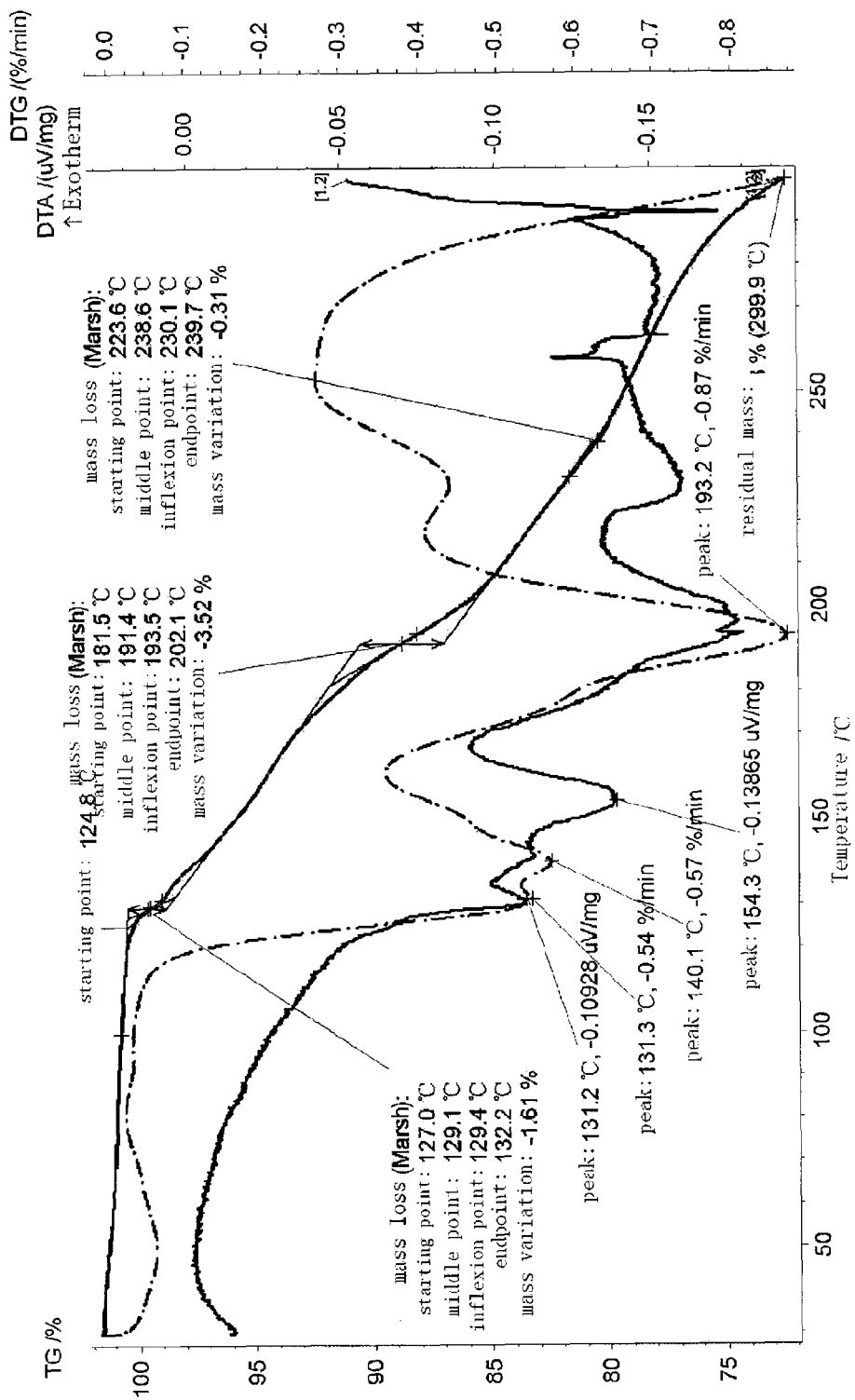
FIG. 3 is the DSC thermal analysis results of the crystalline dimethylamine salt of glyphosate of the present invention.

7. The crystal according to claim 1, wherein said crystal further has the infrared spectrum as substantially shown in FIG. 2 and/or a DSC thermal analysis results as substantially shown in FIG. 3.

8. A process for preparing the crystal according to claim 1, including the steps:
   a) mixing glyphosate powders and an organic solvent under stirring to form a suspension;
   b) introducing a dimethylamine gas into this mixture system to make it undergo a salt-formation reaction, wherein the mole number of the introduced dimethylamine gas is 1.0-3.0 times that of the glyphosate; the reaction temperature is controlled between 5 and 90° C.; and the reaction time is 1.5-5.0 h;
   c) slowly decreasing the temperature to −5-50° C., with a slow stirring, and adding a crystal seed of dimethylamine salt of glyphosate, then resulting in crystals to start precipitating, slowly stirring further till the precipitated crystals grow up, and then separating the crystals.

9. The process according to claim 8, wherein the mole number of the dimethylamine gas is at least 1.0-2.5 times or at least 1.1-1.4 times that of the glyphosate.

10. The process according to claim 8, wherein the reaction temperature is controlled between 5 and 40° C. and the reaction time is 2.0-4.0 h with a white suspending system being formed; the stirring speed is lowered and the temperature is slowly reduced to −5-20° C. and then the precipitated crystalline dimethylamine salt of glyphosate is separated.

11. The process according to claim 10, wherein the reaction temperature is controlled between 25 and 40° C.; the reaction time is 2.5-3.0 h; and then the temperature is slowly reduced to 10-15° C.

12. The process according to claim 8, wherein the reaction temperature is 40-90° C.; the reaction time is 1.0-3.0 h; and a clear solution of the dimethylamine salt of glyphosate is formed; then the stirring speed is lowered, the temperature is slowly reduced to −5-40° C., a crystal seed of dimethylamine salt of glyphosate is added and further stirred for 1.0-2.0 h, and thereafter, the precipitated crystalline dimethylamine salt of glyphosate is separated.

13. The process according to claim 12, wherein the reaction temperature is controlled between 50 and 70° C.; the reaction time is 1.5-2.0 h; and then the temperature is slowly reduced to 15-30° C.

14. The process for preparing a crystalline dimethylamine salt of glyphosate, including the steps:
   a) introducing a portion of a dimethylamine gas into an organic solvent;
   b) adding glyphosate powders under stirring and further introducing the remaining dimethylamine gas into the system, wherein the total mole number of the introduced dimethylamine gas is 1.0-1.4 times that of the glyphosate; the reaction temperature is between 40 and 90° C.; and the reaction time is 1.5-2.5 h; and then obtaining a clear liquid system;
   c) slowly lowering the temperature of the system to 15-25° C. and then adding a crystal seed of dimethylamine salt of glyphosate such that crystals are precipitated; and then separating the precipitated crystalline dimethylamine salt of glyphosate.

15. The process according to claim 8, wherein the organic solvent is selected from the group consisting of monohydric alcohol, dihydric alcohol and trihydric alcohol containing 1 to 6 carbon atoms; tetrahydrofuran, ethyl ether, petroleum ether; acetone, butanone; toluene, xylene, cyclohexane; dichloromethane; ethyl acetate; acetonitrile; DMSO; DMF; and mixtures thereof.

16. The process according to claim 8, wherein the organic solvent is selected from the group consisting of monohydric alcohol and dihydric alcohol containing 1 to 6 carbon atoms; petroleum ether; acetone; toluene, xylene, cyclohexane; dichloromethane; ethyl acetate; and mixtures thereof.

17. The process according to claim 8, wherein the organic solvent is selected from the group consisting of methanol, ethanol, ethylene glycol, propylene glycol, glycerol, cyclohexanol, petroleum ether, toluene, xylene, cyclohexane and mixtures thereof.

18. A solid herbicidal composition comprising the crystalline dimethylamine salt of glyphosate according to claim 1.

19. A solid herbicidal formulation comprising the crystalline dimethylamine salt of glyphosate according to claim 1 and an agriculturally acceptable carrier.

20. The formulation according to claim 19, which is in the form of a powder, a granule or a tablet.

21. The formulation according to claim 19, wherein the carrier comprises an adjuvant and a filler.

22. The formulation according to claim 21, wherein the adjuvant is selected from the group consisting of an alkylpolyglucoside, an aliphatic amine polyoxyethylene ether, a betaine type compound, sarcosine or a sarcosine salt, an aliphatic alcohol ethoxylate, a quaternary ammonium salt surfactant, an alkylamine, an alkylphenol polyoxyethylene ether, an organic silicon adjuvant and the mixtures of two or more of said adjuvants; and/or said filler is selected from the group consisting of a soluble inorganic salt, such as, ammonium sulfate, sodium sulfate, ammonium chloride and the like; kaolin; diatomite; attapulgite; clay; bentonites; argil; carbonwhite; sepiolite; zeolite; talc; agalmatolite and the mixtures of two or more of said fillers.

23. The formulation according to claim 19, comprising by weight:

| | |
|---|---|
| crystalline dimethylamine salt of glyphosate | 20%-90% |
| adjuvant | 5%-30%, and |
| filler | 0%-75%; | based on the total weight of the formulation.

24. A method of controlling weeds or undesirable vegetation, which comprises applying a crystalline dimethylamine salt of glyphosate according to claim 1 dissolved by water to weeds or undesirable vegetation or the growth environment thereof.

25. A method of controlling weeds or undesirable vegetation, which comprises applying the crystalline dimethylamine salt of glyphosate according to the herbicidal composition according to claim 18 to weeds or undesirable vegetation or the growth environment thereof.

26. A method of controlling weeds or undesirable vegetation, which comprises applying a crystalline dimethylamine salt of glyphosate according to the herbicidal formulation according to claim 19 to weeds or undesirable vegetation or the growth environment thereof.

\* \* \* \* \*